United States Patent [19]

Siemer

[11] 4,229,206

[45] Oct. 21, 1980

[54] S-TRIAZINES AS SUGARCANE RIPENERS

[75] Inventor: Sidney R. Siemer, Fresno, Calif.

[73] Assignee: W. R. Grace & Co., New York, N.Y.

[21] Appl. No.: 72,000

[22] Filed: Sep. 4, 1979

[51] Int. Cl.³ .......................................... A01N 43/70
[52] U.S. Cl. ............................................ 71/93; 71/76
[58] Field of Search ...................................... 71/93, 76

[56] References Cited

U.S. PATENT DOCUMENTS 3,925,055  12/1975  MacDonald ............................. 71/93

OTHER PUBLICATIONS

Nickell et al. 1965 Reports–Hawaiian Sugar Technologists—pp. 152–166.

*Primary Examiner*—Catherine L. Mills
*Attorney, Agent, or Firm*—Charles L. Harness

[57] ABSTRACT

Sucrose yield of sugarcane is increased by treating the cane crop a few weeks prior to harvest with a ripening agent comprising an s-triazine.

14 Claims, No Drawings

S-TRIAZINES AS SUGARCANE RIPENERS

BACKGROUND OF THE INVENTION

As sugar is among the principal foods for man and animals, as well as a commercially important food for fermentation organisms, much research is being devoted to raising the sucrose yield of sugarcane in a variety of ways. In recent years this research has increasingly turned toward a search for chemical agents which effectively enhance the ripening of sugarcane and do so in a manner which is both safe and economical.

Some of the more successful chemical ripeners for sugarcane so far discovered are disclosed in U.S. Pat. Nos. 3,224,865; 3,245,775; 3,291,592; 3,482,959; 3,482,961; 3,493,361; 3,505,056; 3,660,072 and 3,671,219. Still other chemical agents which have been found successful or shown promise as sugarcane ripeners, such as cyclo-leucine, anisomycin and cycloheximide, are disclosed, for instance, in Hawaiian Planters' Record, Vol. 58, No. 5, pp. 71–79 (1970).

As is evident from these prior disclosures, the more active ripeners differ widely from each other in terms of chemical structure as well as chemical and biological properties. In the search for effective ripeners failures continue to outnumber successes by a wide margin. Moreover, because of toxicological or ecological concerns and the consequent possibility that rotation of use of different chemical ripeners in consecutive seasons in a given area may be preferable to the continued use of a single ripener mixture, the search for new sugarcane ripeners continues unabated.

Generally speaking, chemicals selected for evaluation are those which have been previously found active in work with other plants as plant hormones, hormonal or non-hormonal herbicides, antifungal agents or antibiotics, growth inhibitors or, contrariwise, growth stimulants. However, among the compounds heretofore known to be useful for such other special and often contradictory purposes only an exceptional few are found to be effective in controlling the ripening of sugarcane in the desired manner.

No predictable relationship has yet been recognized between (a) the chemical structure of such compounds, (b) their phytotoxic effects, or (c) their physiological effects on the morphogenetic development of the plant, on the one hand, and their activity in having positive effects on ripening, on the other hand.

OBJECTS OF THE INVENTION

It is an object of this invention to provide a substance which is economically useful as a chemical ripening agent for sugarcane. A more general object is to increase the sucrose yield of sugarcane by chemically treating it during its maturation prior to harvest without introducing objectionable toxicological hazards. More specifically, it is an object of this invention to increase the sucrose yield of maturing sugarcane by treating a cane crop as the end of their normal maturation cycle or their normal harvest date approaches with a relatively inexpensive material which is sufficiently stable to provide the desired effect over a period of several weeks between application and a variable harvest date, but yet has a relatively low degree of persistence and is susceptible to autodecomposition or to decomposition by soil bacteria. A compound which increases the sucrose content only temporarily over a period of three weeks or less after application and then results in a substantial decrease is usually not a desirable chemical ripener except in situations where harvesting time can be rigidly programmed in advance in relation to the time of application of the chemical ripener.

SUMMARY OF THE INVENTION

According to the present invention the desired objectives have been achieved by the application of a ripening composition comprising an s-triazine as hereinafter defined. More specifically, an excellent increase in sucrose yield has been obtained by applying a spray or dust comprising said s-triazine to sugarcane stalks and leaves in a crop which is nearing the normal maturity stage, and harvesting such crops about 2–10 weeks later. The composition is applied directly to the stalks and leaves by spraying, dusting or the like in order that it be deposited on the stalks and leaves including the younger, growing parts thereof. Experimentally, it can be applied by injection into the spindle.

As is well known, the normal maturation cycle of sugarcane can vary considerably depending on local conditions, from less than 1 year to 3 years or more. For instance, under conditions such as those prevailing in Hawaii sugarcane is normally ripe for harvesting when about 18 to 36 months of age while in other areas of the world sugarcane can be only 9 to 12 months of age when harvested.

The preferred usage form is a mixture containing the s-triazine in an aqueous solution or suspension utilizing one or a combination of known surface active agents commonly and variously used in the prior art as wetting agents, detergents or emulsifying agents. However, dry dusting compositions containing the s-triazine and a solid diluent such as clay are also useful.

In accordance with this invention, a sugarcane crop which is nearing the normal maturity stage is treated with an s-triazine as herein defined or with a composition containing same about two to ten weeks before harvest, the preferred time for treatment being between about four and eight weeks prior to harvest.

Good results are obtained when the sugarcane crop is treated at a rate in the range of from 1 to 4 pounds of an s-triazine as herein defined or equivalent triazine containing composition per acre of sugarcane. However, higher rates (e.g., up to about 30 pounds of s-triazine or more per acre) or rates lower than 1 pound per acre can also be used. The optimum amount will vary somewhat depending on the particular mode of application, environmental conditions, time of year, and age and variety of cane being treated, but can readily be determined for each particular case by preliminary testing.

The active agent is conveniently applied in the field in the form of an aqueous solution, emulsion or suspension, i.e., in a liquid composition which may be sprayed onto the maturing cane plants from a boom-sprayer, or an airplane, or it can be dusted on from an airplane or the like as a dust composition which contains the active compound diluted with an inert solid such as clay.

In preparing suitable liquid composition, surface active agents of the type described, for instance, in U.S. Pat. No. 3,224,865, column 2, lines 61–66 or in U.S. Pat. No. 3,245,775, column 2, lines 57–64 are convenient to use. The preferred surfactants for use in liquid compositions of the present invention are those of the non-ionic type, e.g., alkyl phenoxy poly(ethyleneoxy)ethanols such as adducts of nonylphenol and ethylene oxide; trimethyl nonyl polyethylene glycol ethers; polyethylene oxide adducts of fatty and resin acids, and long chain alkyl mercaptan adducts with ethylene oxide. The surfactant (surface active agent) is not critical.

With the type of spray apparatus used in this work, it has been found convenient to apply the product to the sugarcane field in the form of an aqueous solution, suspension or emulsion having a concentration of active agent such that the application at the rate of from 5 to 20 gallons of liquid composition per acre will provide the required dosage of active chemical. However, the use of lower or higher gallonages may be preferred when a different dispensing mechanism is used.

The preferred carrier for the active ripening agent is water to which about 0.1 to 2 percent by weight of surface active agent has been added. However, instead of using water as the carrier, non-phytotoxic mineral oils either as such or in the form of water-in-oil or oil-in-water emulsions may be used similarly in accordance with practices which are otherwise well known in the art of treating vegetation in the field with beneficial growth control agents. Excellent results are obtained when the s-triazine is present as essentially the sole active ingredient in the treating composition, but it may also be applied in combination with other ripeners.

The s-triazines as a genus are well known, as well as methods for their synthesis. A typical synthesis starts with cyanuric chloride. Two of its three chlorines are quite reactive and react readily with compounds carrying an amino group with one or two active hydrogens. A base such as NaOH or an amine is added to react with liberated HCl. The reaction is done at temperatures of 20°–50° C. Such reaction replaces two chlorines with the same amine or amine derivative. If two different substituents are desired, the first Cl is replaced with a first amine substitutent at low temperature, e.g., −15° to 0° C., followed by replacing the other Cl with the second substitutent, suitably at a higher temperature, e.g., 20°–50° C. More detailed procedures for synthesis of the s-triazines is given in Kirk-Othmer, Encyclopedia of Chemical Technology, 2d Ed., 22, 183 ff.

The s-triazines are not strangers to agriculture. In the past, however, they have been used mainly as herbicides. The 2-chloro derivatives are of major commercial importance in this field. Such derivatives include, e.g., Atrazine, Simazine, Propazine, and Chlorazine. The success of these materials is considered due to their ability to interfere with photosynthesis. Simazine, 2-chloro-4,6-bis(ethylamino)-s-triazine inhibits the formation of sugars. Ann. Rev. Plant Physiol. 14, 353 (1963). They inhibit the Hill reaction (an indication of herbicidal activity). Nature 139, 881 (1937); Ibid., 146, 61 (1940). In 1965 Reports, Hawaiian Sugar Technologists, Effects of Chemicals on Ripening of Sugarcane, by Nickell et al., pp. 152–166, 2-chloro-4-(dimethylamino)-6-(isopropylamino)-s-triazine is stated (at p. 162) to have slight but definite activity. So far as is known this is the only triazine ever previously tested for sugarcane ripening activity.

The s-triazines contemplated for use in this invention have the following formula:

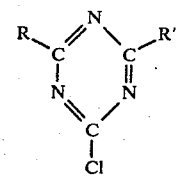

in which R is

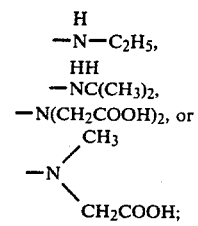

and R' is independently selected from the group consisting of

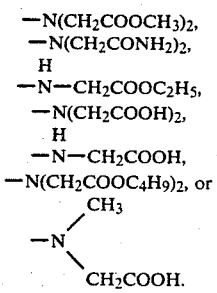

Field Treatment

Test Procedure

The following test procedure was used to obtain the data reported in the Table.

A. Sugarcane Plant Selection and Labeling

Prior to establishing testing in the fields used, untreated duplicant samples were taken at 100-ft. intervals over the entire length of the three fields (1320 ft. long). With the exception of definite differences between varieties, there was little variation between stalks over the length of the field. As the season progressed, age of the stalk played a role in ripening readings, strongly suggesting that only immature primaries be worked with or immature secondary stalks be worked with in late testing. This was done.

Three different varieties, selected because of their non-closely related genetics, were all treated with spindle treatments. The three varieties were CL-41-223, CL-54-378 and CL-59-1052. Treatments of all varieties were conducted on the outside two rows for ease of accessibility. Selected stalks were labeled with three colors of plastic tape: red, for the high rate, blue, for the median rate, and green, for the lowest rate. In the spindle tests, three replicate plants were tagged with each color, while in spray tests the beginning and end were identified—about 10 ft. of row. The date of application and treatment code number were indelibly inscribed on the tape.

B. Spindle Treatment

Plants were selected for equal height and size (7–9 leaves), grouped into three treatment rates and replicates of three. The three rates selected for application addition of the s-triazines were 10, 1, and 0.1 mg/plant. The compounds were weighed in the laboratory directly into 20-oz. polyethylene bottles and shipped undiluted to the field. A water solution containing 1% Tween 20 was made up in the lab, shipped to the field, and added in the field. Dilutions used gave 10, 1 and 0.1 mg. per plant when applied in 0.3 ml. Acetone or isopropyl alcohol were used when solubility problems arose. A volume of 0.3 ml. per plant was used. Injections into the spindle were made with either an 18 or 20-gauge needle and a 1.0 cc syringe.

Observations, such as leaf discoloration, injury to foliage or spindle, were made weekly.

C. Foliar Treatment

Compounds were prepared for foliar spraying in the field in the same general way as those used for spindle application. Larger amounts of compound and greater volumes were used to allow spraying. Three rates were used, viz., 8, 2 and 0.5 lbs. active ingredient ("A. I.") per acre. Sixty gallons of spray was found more desirable than 15 or 30 when applied by hand sprayer at 3 mph because the spray droplets were larger and more controllable. Better coverage resulted and spraying was not as easily disrupted or distorted by wind.

Ten feet of row was labeled with tape for each compound, with each treated area separated from another by about four feet. This is idealized, since separation may be 20 feet or more depending on stand quality.

The spray equipment used for making applications included a $CO_2$ pressure tank and A. I. container on a back pack, plus a spray wand. Prior to spraying, the 330 mls. of compound solution was placed in a 16-oz. plastic container. The bottle cap had two holes cut through it—one to allow a tube to enter and extend to the bottom of the bottle, and the other to allow pressurized gas to enter. A piece of plastic wrap was placed under the cap prior to spraying to prevent spillage. This was pierced when the container was placed into the spray head. The container was placed into the bottom of the stainless steel canister and the retaining cap screwed tightly into place. The $CO_2$ line from the back pack tank was attached to the canister held on the ammunition belt around the person doing the spraying. When the valve was depressed, $CO_2$ pressurized the canister and spray emitted from the nozzles. Spraying was accomplished by walking at 3 mph (pre-calibrated), starting several feet before reaching the area to be treated. When the tape marker at the beginning of the plot was passed, the $CO_2$ valve was actuated and spraying began. Spraying was continued until the container in the canister was empty. Acetone was placed in the container and pressurized to clean the system before spraying the next compound.

D. Evaluation Procedure

Four weeks after application, cane stalks were cut from the field with lopping shears with sufficient length to assure sampling of ten internodes counting back from the growing tip. Generally, cane from six or eight treatments of the highest rate was cut first. Leaves were stripped from the stalk at the point of sampling and carried to the evaluation table. A juice sample was squeezed from the internode tissue sections using a modified pair of pliers (small plates welded to the jaws). The juice was deposited directly onto a hand-held, temperature-compensated, refractometer and the percent soluble solids (Brix) read and recorded. The refractometer was dipped into a beaker of clear water, removed and wiped dry with a paper towel, and thus made ready for the next sample. If the Brix readings from a treatment warranted, the median rate would be evaluated, and likewise, the low rate. Generally, untreated readings were 4.5–5.5, depending on variety.

EXAMPLE 1

(Log 2008 in the Table)

Following the above Test Procedure (spindle application) an s-triazine of the formula

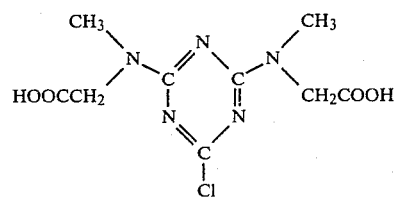

was dissolved in water with "Tween-20" surfactant at 10 mg. A.I. per plant, using the three varieties indicated. (Tween 20, a nonionic surfactant, is a polyoxyethylene derivative of the monolaurate ester of sorbitan fatty acid. (It is available commercially from ICI United States, Inc.) After four weeks Brix readings were taken for treated and untreated plants to determine sucrose content as described in the Test Procedure, and the ratio of Brix readings of treated plants to Brix readings for untreated plants determined arithmetically. Obviously, if the ratio exceeds unity, the inference is that the increased sugar (i.e., ripening) was caused by the A.I. The results showed ratios substantially in excess of one on all three varieties. These results, together with others, are reported in the Table. Not all compounds gave improved results for each of the three varieties. However, every one of the compounds showed improved ripening for at least one of the varieties.

Three well-known commercial ripeners (Roundup, Polaris, and Embark) were tested under the same conditions, and results for them are given.

Summary treated/untreated ratios of brix readings for the indicated treatments recorded 4 weeks after treatment by spindle application (10 mg/plant) to three sugarcane varieties (A,B,C)[1] grown in Florida

| Log No. | $R'^2$ | $R^2$ iPr NH | | | EtNH | | |
|---|---|---|---|---|---|---|---|
| | | A | B | C | A | B | C |
| 2036 | $N-(CH_2COOMe)_2$ | — | — | — | 1.277 | 1.690 | 1.400 |

-continued

Summary treated/untreated ratios of brix readings for the indicated treatments recorded 4 weeks after treatment by spindle application (10 mg/plant) to three sugarcane varieties (A,B,C)[1] grown in Florida

| Log No. | R'[2] | i Pr NH A | B | C | EtNH A | B | C |
|---|---|---|---|---|---|---|---|
| 2086 | N—(CH₂CONH₂)₂ | — | — | — | .768 | 1.461 | .893 |
| 2037 | H—N—CH₂COOEt | .806 | .761 | 1.180 | 1.104 | 1.651 | 0.917 |
| 2028 | N—(CH₂COOH)₂ | 1.060 | .992 | 1.058 | 1.091 | 1.558 | 1.135 |
| 2031 | H—N—CH₂COOH | 1.085 | 1.497 | 1.181 | 1.112 | 1.208 | 1.130 |
| 2032 | N—(CH₂COOBu)₂ | .979 | 1.492 | .960 | | | |
| 2009 | R N—(CH₂COOH)₂ R' N—(CH₂COOH)₂ | 1.061 | 1.885 | 1.034 | | | |
| 2008 | R CH₃—N—CH₂COOH R' CH₃—N—CH₂COOH | 1.108 | 1.518 | 1.533 | | | |
| 2002 | Roundup Standard | 1.404 | 2.008 | 2.356 | | | |
| 2061 | Polaris Standard | 1.219 | .883 | 2.312 | | | |
| 2062 | Embark Standard | 1.177 | .982 | 1.203 | | | |

[1] A = CL-54-378  B = CL-59-1052  C = CL-41-223

[2] R and R' in: 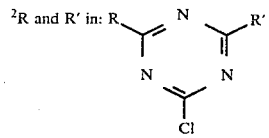

Although the experiments were done by spindle application, the same improvements will be achieved by foliar application, as described in the Test Procedure. For commercial use in the field foliar application would of course be employed.

In commercial operation the A.I. is applied by foliar application, by spraying an aqueous solution or suspension of the s-triazine, at a time from about 2 to 10 weeks prior to harvest, and preferably when the plants are between about 18 and 24 months of age. The aqueous composition preferably contains about 0.6 to 16 wt.% A.I., about 0.1-2 wt.% nonionic surfactant, and is sprayed at the rate of about 5 to 20 gallons of aqueous composition per acre.

I claim:

1. A process for modifying the ripening of sugarcane plants so as to increase their yield of sucrose which comprises applying an s-triazine in a sucrose increasing amount directly to the cane plants as hereinafter specified at a time from about 2-10 weeks prior to harvest; said s-triazine having the formula

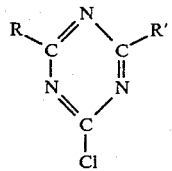

(a) in which R is EtNH—, R' is —N(CH₂COOMe)₂, and the sugarcane variety is CL-59-1052 or CL-41-223;
(b) in which R is EtNH—, R' is —N(CH₂CONH₂)₂, and the sugarcane variety is CL-59-1052;
(c) in which R is EtNH—, R' is —HNCH₂COOEt, and the sugarcane variety is CL-59-1052;
(d) in which R is EtNH—, R' is —N(CH₂COOH)₂, and the sugarcane variety is CL-59-1052;
(e) in which R is iPrNH—, R' is —HNCH₂COOH, and the sugarcane variety is CL-59-1052;
(f) in which R is iPrNH—, R' is —N(CH₂COOBu)₂, and the sugarcane variety is CL-59-1052;
(g) in which R and R' are —N(CH₂COOH)₂, and the sugarcane variety is CL-59-1052; or
(h) in which R and R' are —N(CH₃)CH₂COOH, and the sugarcane varieties are CL-59-1052 or CL-41-223.

2. A process according to claim 1 wherein the s-triazine is sprayed onto the cane plants as a liquid composition containing water as a carrier.

3. A process according to claim 2 wherein the s-triazine is applied to the cane plants as an aqueous solution or suspension at the rate of about 3 to 20 gallons of aqueous composition per acre.

4. A process according to claim 3 wherein the cane plants are between 18 and 24 months of age when the s-triazine is applied thereto.

5. A process according to claim 3 wherein the aqueous composition contains about 0.6 to 16 percent by weight of an active ingredient.

6. A process according to claim 5 wherein the aqueous composition contains a surface active agent.

7. Process according to claim 1 in which R is EtNH—, R' is —N(CH₂COOMe)₂, and the sugarcane variety is CL-59-1052 or CL-41-223.

8. Process according to claim 1 in which R is EtNH—, R' is —N(CH₂CONH₂)₂, and the sugarcane variety is CL-59-1052.

9. Process according to claim 1 in which R is EtNH—, R' is —HNCH₂COOEt, and the sugarcane variety is CL-59-1052.

10. Process according to claim 1 in which R is EtNH—, R' is —N(CH₂COOH)₂, and the sugarcane variety is CL-59-1052.

11. Process according to claim 1 in which R is iPrNH—, R' is —HNCH₂COOH, and the sugarcane variety is CL-59-1052.

12. Process according to claim 1 in which R is iPrNH—, R' is —N(CH₂COOBu)₂, and the sugarcane variety is CL-59-1052.

13. Process according to claim 1 in which R and R' are —N(CH₂COOH)₂, and the sugarcane variety is CL-59-1052.

14. Process according to claim 1 in which R and R' are —N(CH₃)CH₂COOH, and the sugarcane varieties are CL-59-1052 or CL-41-223.

* * * * *